US012605275B2

(12) United States Patent
Santos

(10) Patent No.: US 12,605,275 B2
(45) Date of Patent: Apr. 21, 2026

(54) HEAT THERAPY SYSTEM USING ARRAY OF INSULATED PROBES APPLIED PER SYSTEM'S UNIQUE PARAMETERS

(71) Applicant: Rogelio L. Santos, Fairfield, CA (US)

(72) Inventor: Rogelio L. Santos, Fairfield, CA (US)

( * ) Notice: Subject to any disclaimer, the term of this patent is extended or adjusted under 35 U.S.C. 154(b) by 437 days.

(21) Appl. No.: 18/236,373

(22) Filed: Aug. 21, 2023

(65) Prior Publication Data

US 2025/0064630 A1     Feb. 27, 2025

(51) Int. Cl.
*A61F 7/00*     (2006.01)
*A61F 7/02*     (2006.01)
*H05B 1/02*     (2006.01)

(52) U.S. Cl.
CPC .............. *A61F 7/007* (2013.01); *A61F 7/02* (2013.01); *H05B 1/025* (2013.01); *A61F 2007/0002* (2013.01); *A61F 2007/0018* (2013.01); *A61F 2007/0029* (2013.01); *A61F 2007/0039* (2013.01); *A61F 2007/0093* (2013.01); *A61F 2007/0096* (2013.01); *A61F 2007/0282* (2013.01)

(58) Field of Classification Search
CPC ........... B29C 41/28; B29C 55/00; B29D 7/01; A61F 2007/0002; A61F 2007/0018; A61F 2007/0029; A61F 2007/0039; A61F 2007/0071; A61F 2007/0086; A61F 2007/0087; A61F 2007/0093; A61F 2007/0095; A61F 2007/0096; A61F 2007/0282; A61F 7/007; A61F 7/02; H05B 1/025
See application file for complete search history.

(56) References Cited

U.S. PATENT DOCUMENTS

2015/0032192 A1*  1/2015  Pezzi ...................... A61F 7/007
                                                    607/104
2018/0360648 A1*  12/2018  Press ....................... A61F 7/007
2023/0090085 A1*  3/2023  Dai .......................... A61H 1/00
                                                    601/18

* cited by examiner

*Primary Examiner* — Tigist S Demie
(74) *Attorney, Agent, or Firm* — Richard Bennett Salles

(57)     ABSTRACT

The invention is, inter alia, an electrically powered heating pad/rod/probe/cubic that utilizes variously-sized probe tips (geometric shaped substantially-solid "elements," "rods," "cubics" or "probes," which are versatile and effective in poking/massaging different parts of the human body. The apparatus device and system is intended for medical purposes, providing heat therapy for body surfaces. The probes are capable of maintaining an elevated temperature during use, substantially dependent on the body part and other sensory feedback. The invention is used, inter alia, for warming of desired parts of the human body in order to alleviate and manage body pain. The localized application of the heat causes the blood vessels in (and underneath) that area to dilate, enhancing perfusion to the targeted tissue. The system involves proper thermal poking/application of specially-tailored geometric-shaped heating rods (aka "probe heads, or "cubics") which are securely covered with disposable covers [ideally cotton/polyester/spandex and amalgams thereof] disposable fabric] which allows good hygiene and sanitation during repeated use. The device's cubics are each equipped with a central-core resistive heating element; the device/system comprises an automatic shut off feature and protective alarm—&—circuitry to properly respond to over-current & overvoltage.

1 Claim, 11 Drawing Sheets

200

| DESCRIPTION | |
|---|---|
| Various Shaped "Threaded Solid Aluminum Cubics Heating Pad" ("TSAHP") | RECOMMENDED BODY PARTS TO USE |
| Small Concave "TSAHP" Tip | FINGERS, KNUCKLES, TOES |
| Medium Concave "TSAHP" Tip | ELBOW, KNUCKLES, BACK BONE AREA |
| Big Concave "TSAHP" Tip | ELBOWS, KNEES, SHOULDERS, NAPE |
| Small Flat "TSAHP" Tip | FINGERS, TOES |
| Medium Flat "TSAHP" Tip | FACE, BACK, ARMS, LEGS |
| Big Flat "TSAHP" Tip | BACK, THIGH, NECK ARMS, LEGS, FACE, CHEST, SIDE BODY, HIPS |
| Small Pointed "TSAHP" Tip | FINGERS, TOES |
| Medium Pointed "TSAHP" Tip | NECK, FINGERS, TOES, PALM, SOLE |
| Big Pointed "TSAHP" Tip | NECK, BACK, THIGH, BUTTOCKS, HIPS |
| Small Round "TSAHP" Tip | NECK, FINGERS, TOES, PALM, SOLE |
| Medium Round "TSAHP" Tip | NECK, ARMS, LEGS, BACK, CHEST |
| Big Round "TSAHP" Tip | NECK, ARMS, LEGS, BACK, CHEST |

FIG. 9

HEAT THERAPY SYSTEM USING ARRAY OF INSULATED PROBES APPLIED PER SYSTEM'S UNIQUE PARAMETERS

This application claims priority to U.S. Provisional Application 63,399,830 Filed Aug. 21, 2022.

TECHNICAL FIELD OF THE DISCLOSURE

This application relates to the field of heat therapy devices, methods and systems.

BACKGROUND OF THE DISCLOSURE

Heat therapy systems for muscle problems and various organ, joint, ligament, fascia, vascular, endocrine, nervous and circulatory issues customarily depend on a healthcare professional taking their "best guess" at where to place soft heating pads, how long to hold the heat on the skin above a joint, muscle or organ, and what kind of "heating pad" to use. Health professionals do not currently have specially tailored heating rods to apply to particular body parts for particular periods of time-&-temperature based on an electronically controlled-and-applied System with specially tailored apparatus-devices for this purpose.

What is needed is a system supplying specially-tailored heating probes, or "cubics," applied according to precise parameters, namely specific temperatures for precise time periods for particular body parts, and an apparatus device to control and execute these applications with appropriate application, adjustment-capacity and cut-off mechanisms. The herein-disclosed invention solves these issues.

SUMMARY

The invention is, inter alia, a powered heating pad that utilizes variously-sized probes (geometric shaped substantially-solid "elements," "rods," "cubics" or "probes," which are versatile and effective in poking/massaging different parts of the human body. The apparatus device and system is intended for medical purposes, providing heat therapy for body surfaces. The probes are capable of maintaining an elevated temperature during use, substantially dependent on the body part and other sensory feedback. The invention is used, inter alia, for warming of desired parts of the human body in order to alleviate and manage body pain. The localized application of the heat causes the blood vessels in (and underneath) that area to dilate, enhancing perfusion to the targeted tissue. The system involves proper thermal poking/application of specially-tailored geometric-shaped heating rods (aka "probe heads, or "cubics") which are securely covered with disposable covers [ideally cotton/polyester/spandex and amalgams thereof] disposable fabric] which allows good hygiene and sanitation during repeated use. The device's cubics are each equipped with a central-core resistive heating element; the device/system comprises an automatic shut off feature and protective alarm—&—circuitry to properly respond to overcurrent & overvoltage.

(*note that Aluminum can be any appropriate solid material with conductive property, and that Pad can be described as probe/tip $400$/head)

Herein (FIG. 7) grouped by head $400$ shape:
$410s$ & $420s$ for convex heads/tips of different diameters;
$430$'s for cubic heads with substantially flat tip [with slight beveled/chamfered edge for comfort] of different sizes/diameters,
$440s$ for tips with concave tips with different sizes/diameters) in one aspect of the invention.

Figure 8:
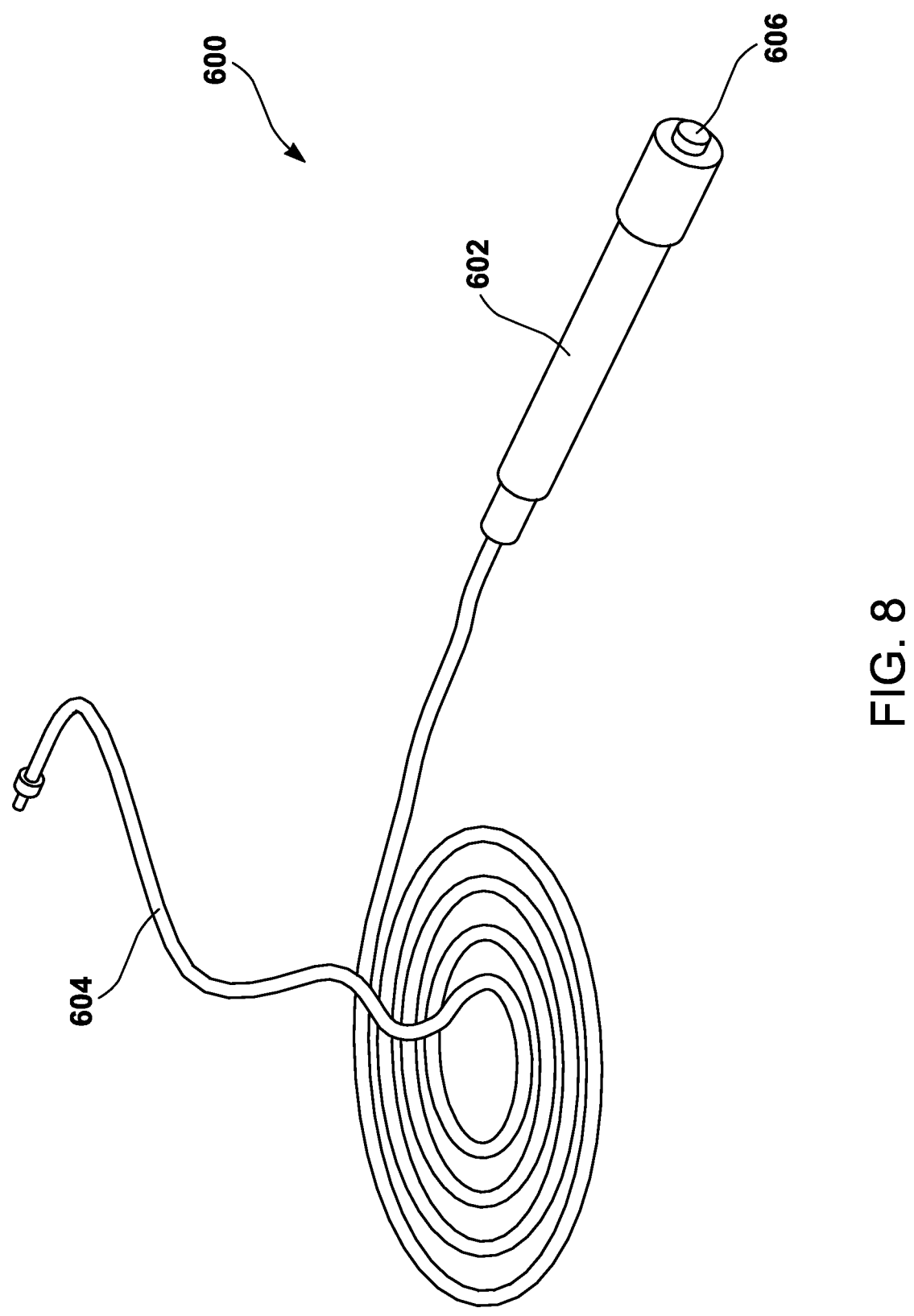

FIG. 8 is a perspective view of the sensory rod $600$, the hand-held subject feedback paddle $600$, featuring the alarm/beep button $606$ and holder $602$ and cord $604$, in one aspect of the invention.

FIG. 9 is a chart describing the System's parameters-prompts illustrating which "TSAHP/cubic tip $400$" is applied-to/designed-for which body part, in on aspect of the invention.

Figure 10:
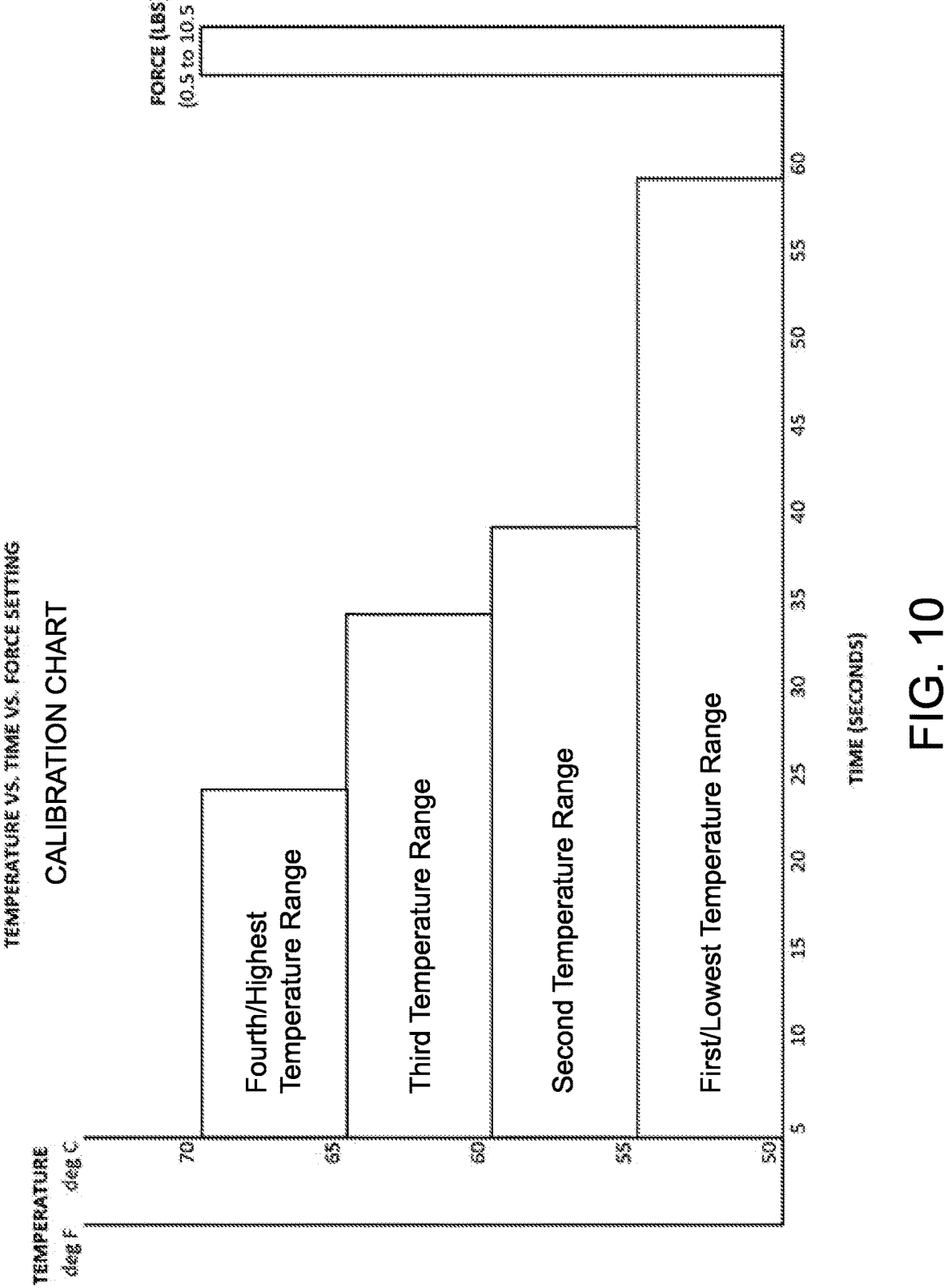

FIG. 10 is a chart describing the System's parameter-prompts-guidelines for proper application of the cubics' temperature, time and force in one aspect of the invention.

DETAILED DESCRIPTION OF THE DRAWINGS

Figure 1:
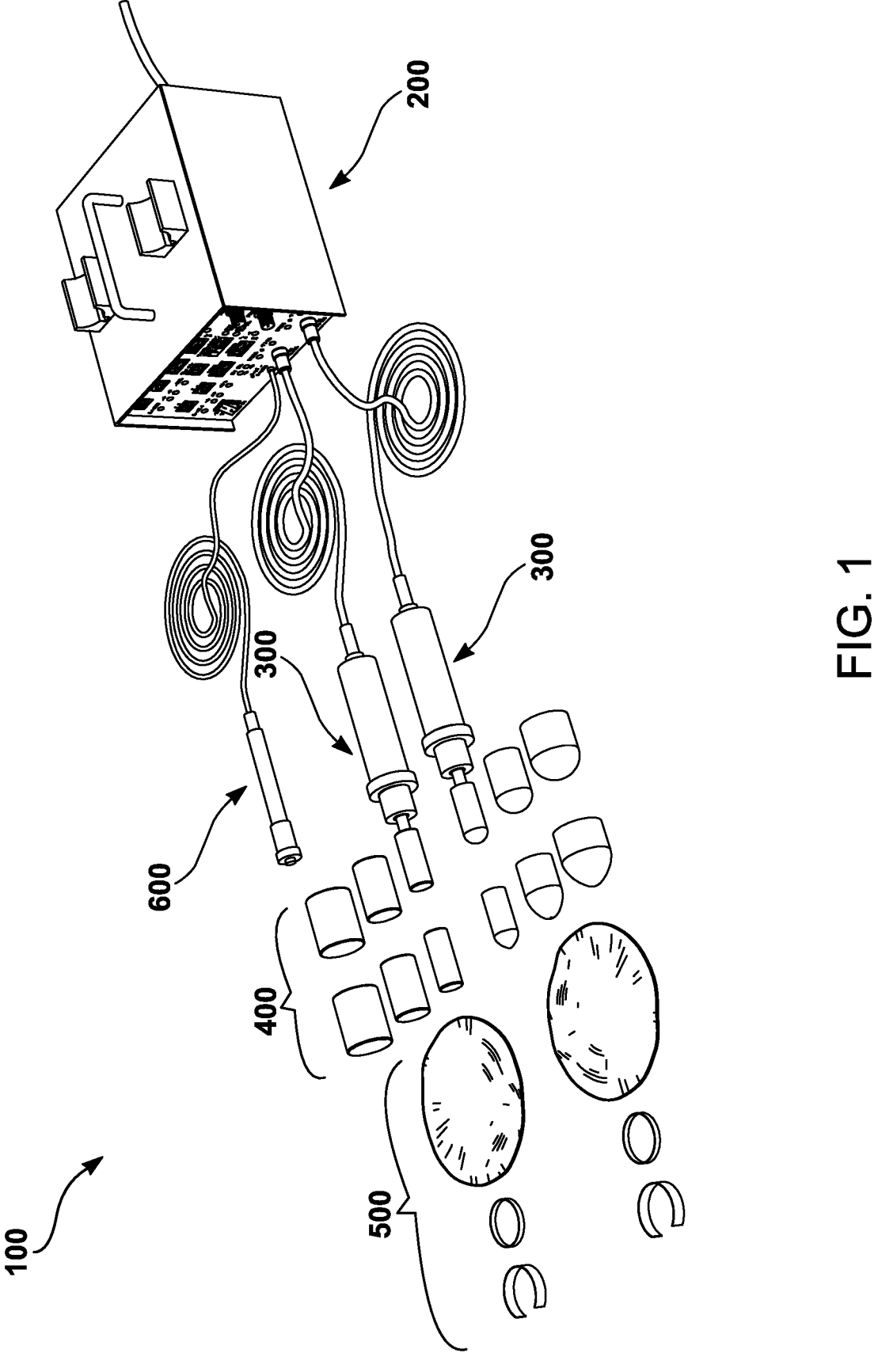
FIG. 1 illustrates a schematic overview of many of the relevant components of the present invention, "partially assembled," [parts substantially separated to show internal components] in one aspect of the invention.
Figure 2:
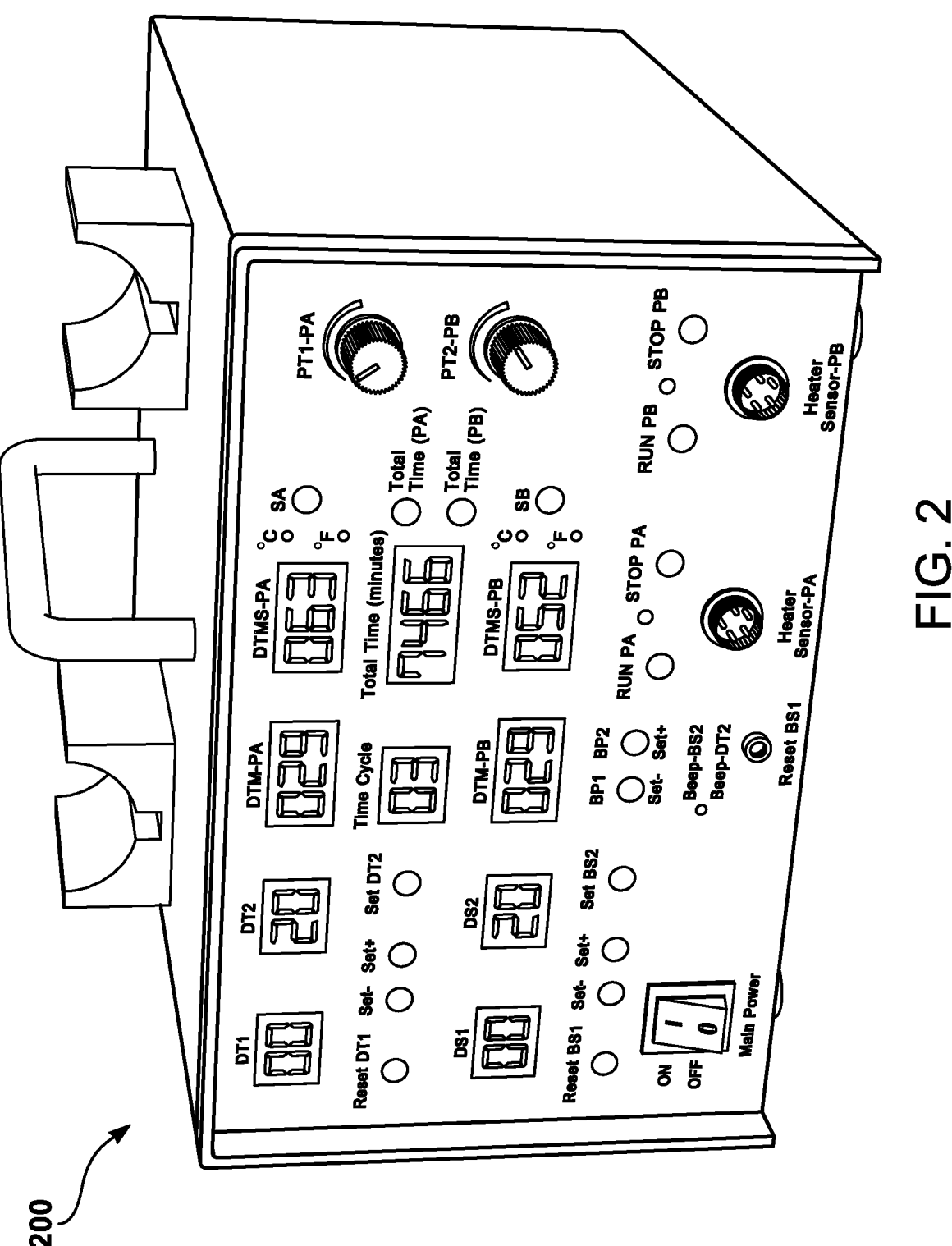
FIG. 2 is a perspective view of the system's Controller, esp. front, highlighting front channels, heating level nobs, on/off switch, timer buttons, heat and time readouts, etc. in one aspect of the invention.

FIG. 1 illustrates a schematic overview of the majority of relevant components of the present invention, herein shown "dis-assembled," with the primary components laid out for view, comprising, inter alia, The control box $200$;
Two heater cubics/probes $300$;
One sensory rod, the hand-held feedback paddle $600$;
An array of cubic heads $400$/tips/"TSAHPs;
The cubic cover apparatus' $500$, including inter alia,
Two Disposable Insulative Fabric Covers $502$;
Two Elastic Band $504$ to Secure Firmly the Insulative Fabric Covers $502$
VELCRO™ $506$-style cinchs to Double Protect the Insulative Fabric Covers $502$ FIG. 2 illustrates the controller heater panel (UNIT) components and operations in one embodiment of the system.

*The "Cubic" is a solid "element" (aluminum metal) geometric figure that is attached at the frontal end of the PTFE/Tip 400 poking probe and when covered 502 with cotton/polyester/spandex fabric will become the heating pad/tip 400.

*Note: The Solid Element used in this present invention is, inter alia, in one embodiment, Aluminum metal. The word "Solid Element" is intermittently used so later Solid amalgam-type "elements" may be used, inter alia stainless steel, copper metal, glass, rubber, etc.

The unit comprises, inter alia:

SELECTOR VOLTAGE (DUAL VOLTAGE-120/240VAC).

POWER INPUT-MALE SOCKET (L1-N-GROUND/L1-L2-GROUND);

FUSE FOR THE AC POWER (4 Amps, 250 VAC)

MAIN POWER SWITCH

RED LED LIGHT WHEN POWER IS ON

ON/OFF—SWITCH FOR MAIN POWER

HEATER/SENSOR PA—CHANNEL PA

TO RUN CHANNEL PA—PUSH GREEN BUTTON RUN PA TO INITIATE HEATER/SENSOR PA—CHANNEL PA TO RUN;

GREEN LED WILL LIT WHEN RUN BUTTON PA IS PUSHED;

CHANNEL PA—5-PIN CONNECTOR (MALE);

PIN 1 & 2 (CARTRIDGE HEATER, 80 WATTS, 24 V)

PIN 3 (GROUND)

PIN 4 & 5 (SENSOR, THERMOCOUPLE)

TO STOP CHANNEL PA—PUSH RED BUTTON STOP PA;

RED LED WILL LIT DURING HEATER/SENSOR-PA IS AT STOP OR NOT RUNNING;

HEATER/SENSOR PB—CHANNEL PB;

TO RUN PB—PUSH GREEN BUTTON RUN PB TO INITIATE HEATER/SENSOR PB TO RUN;

GREEN LED WILL LIT WHEN BUTTON RUN PB IS PUSHED;

PB—5-PIN CONNECTOR (MALE)

PIN 1 & 2 (CARTRIDGE HEATER, 80 WATTS, 24 V)

PIN 3 (GROUND)

PIN 4 & 5 (SENSOR, THERMOCOUPLE)

TO STOP PB—PUSH RED BUTTON STOP PB TO STOP HEATER/SENSOR PB—CHANNEL PB;

RED LED WILL LIT DURING HEATER/SENSOR PB IS STOP OR NOT RUNNING;

TEMPERATURE CONTROL OF HEATER/SENSOR PA

PT1-PA—POTENTIOMETER TO ADJUST THE TEMPERATURE OF HEATER/SENSOR PA BY X1 INCREMENT; SA DEG ° C.—PUSH THE SA BLUE BUTTON (#6), DEG ° C. LED WILL LIT FOR THE DEG ° C. READING AT DTMS-PA;

SA DEG ° F.—PUSH THE SAME SA BLUE BUTTON, DEG ° F. WILL LIT FOR THE DEG ° F. READING AT DTMS-PA;

DTMS-PA—SET DIGITAL TEMPERATURE READING FROM PT1-PA

DTM-PA—ACTUAL DIGITAL TEMPERATURE READING OF HEATER/SENSOR PA DURING OPERATION;

TEMPERATURE CONTROL OF HEATER/SENSOR PB

PT2-PB—POTENTIOMETER TO ADJUST THE TEMPERATURE OF HEATER/SENSOR PB BY X1 INCREMENT;

SB DEG ° C.—PUSH THE SB BLUE BUTTON, Deg ° C. LED WILL LIT FOR THE DEG ° C. READING AT DTMS-PB;

SB DEG ° F.—PUSH THE SB BLUE BUTTON, Deg. ° F.

LED WILL LIT FOR THE DEG ° F. READING AT DTMS-PB;

DTMS-PB—SET DIGITAL TEMPERATURE READING FROM PT1-PB;

DTM-PB—ACTUAL DIGITAL TEMPERATURE READING OF HEATER/SENSOR PB DURING OPERATION;

DIGITAL TIMER FOR POWER OFF FOR HEATER/SENSOR PA AND HEATER/SENSOR PB;

SET-DT2-TO SET DT2 TIMER, PUSH BUTTON SET-DT2 (#13), DIGITAL DT2 READING KEEPS BLINKING READY TO SET, THEN, PUSH FOR BUTTON SET-FOR DECREMENT and SET+ (#14) FOR INCREMENT, THEN SET TO DESIRED TIME WHEN TO SWITCH OFF HEATER/SENSOR-PA AND HEATER/SENSOR-PB DT2—DIGITAL (RED) LED TIMER READING AT SET POINT (99 MINUTES MAXIMUM SETTING TIME);

DT1—DIGITAL (RED) LED FOR THE ELAPSED TIME OF DT2 (99 MINUTES MAXIMUM), HEATER/SENSOR PA AND HEATER/SENSOR PB AUTOMATICALLY SWITCHED OFF WHEN DT1 REACHES READING OF DT2;

RESET DT1—RESETTING DT1 TIME TO ZERO AT ANYTIME;

BEEPING TIMER (SECONDS)—(WHEN MOVING THE THERMAL PROBE TO OTHER SPOT)

BS2—DIGITAL LED TIMER READING IN SECONDS (99 SECONDS MAXIMUM)

BS2 SETTING—PUSH SET BS2 (#25) WHEN BS2 IS BLINKING, THEN PUSH SET-(FOR DECREMENT) OR SET+ (FOR INCREMENT) TO DESIRED BS2 TIME.

BS1—DIGITAL LED REPETITIVE TIMER, WHEN BS1REACHES THE SET TIME FOR BS2, BS1 WILL RESET TO ZERO AND COUNT AGAIN, BS1 WILL RESET TO ZERO UPON RECHING BS2 READING AGAIN AND AGAIN, AND SO ON;

RESET BS1—TO RESET BS1 TO ZERO (0), PUSH RESET BS1 ANYTIME TO RESET BS1 AT ZERO READING

TIME TOTALIZER FOR HEATER/SENSOR-PA AND HEATER/SENSOR-PB

Total Time (minutes)—This is the Total Time Reading for any of the HEATER/SENSOR-PA AND HEATER/SENSOR-PB Time Used—After a Total Time—MAXIMUM OF 9999 MINUTES HAD ELAPSED, Total Time (minutes) will RESET TO ZERO AND TIME CYCLE WILL COUNT ONE, THEN COUNT 2, 3, 4 AND SO ON, when Total Time (minutes) Maximum of 9999 minutes had elapsed Total Time PA—PUSHING THE BUTTON Total Time PA, Total Time (minutes) WILL DISPLAY THE TOTAL TIME THE HEATER/SENSOR-PA HAD OPERATED Total Time PB—PUSHING THE BUTTON Total Time PB—Total Time (minutes) WILL DISPLAY THE TOTAL TIME THE HEATER PB HAD OPER-ATED

BEEPING SOUNDS

BEEP DT2—THERE WILL BE THREE (3) BEEPS SOUND WHEN DIGITAL TIMER SET FOR DT2 AND DT1 HAVE ELAPSED

BEEP BS2—THERE WILL BE ONE (1) BEEP SOUND FOR EVERY CYCLE OF TIME SET FOR BS2

BP1-SET–PUSHING BP1-SET–BUTTON WILL DECREASE BEEP SOUND UNTIL NO BEEP

BP2-SET+(#37), PUSHING BP2-SET+BUTTON WILL INCREASE BEEP SOUND UNTIL MAXI-MUM

NOTE:

HEATER CARTRIDGES HAVE FIVE WIRES a) Two (2) wires for the Heater, b) Two wires for the thermocouple-sensor and c) one wire for the ground HEATER CARTRIDGE SPECS for each; 80 WATTS, 24 VOLTS, with Electric Resistive Elements pro-ducing heat Length of Heater Cartridge Wires to the 5-pin male socket #2 is 180 mm;

HEATER CARTRIDGE DIMENSIONS—8.79 mm-Di-ameter×110 mm Length

ELECTRONIC METAL BOX DIMENSIONS—5¼"-Height×8"-Length×9"-Depth (inches)

ELECTRONIC CONTROL BOX 200:1.2 mm thick, Black Iron

Soldering of electronic parts: Lead-Free

Paint of the Electronic Control Box—Lead-Free

Length of the 120/240VAC Input Cables=2.5 meters

Length of the Cables from Electronic Box 5-pin male socket #1 to the

TEFLON (PTFE) Thermal Probe male socket #2=2.5 meters

Both ends of the Cables from Heater Box to the PTFE Thermal Probe will have a 5-Pin female socket #1 & #2 connected to the 5-pin male sockets #1 and #2 (#1 connected to 5-pin male socket #1 at the heater box and the other #2 connected to the 5-pin male socket #2 at the heater cartridge).

Colors of the Electronic Control Box:

1) Black, 2) Sky blue, 3) Green, 4) Red, 5) Yellow, 6) White, 7) Silver and 8) Gold The Temperature range of the Heaters will be from ambient temperature DEGREES ° C., then programmable 80 to 120 DEGREES ° C. max.

Temperature fluctuation + or –3 DEGREES ° C.

Transformer Rating: 1Phase, 50 HZ/60 HZ, 200 VA, 110 VAC/220 VAC

Primary, 24 VAC/6 VAC Secondary

Please see attached drawing and specifications of the;

a) TEFLON (PTFE) Thermal Probe, b) Cartridge Heater (Resistive Element Heater), c.) Various Sizes of Solid Aluminum Cubics Heating Pad Please note also that the Powered Heating Pad has cir-cuitries and alarm for short circuit current, over voltage and properly grounded.

Figure 3:
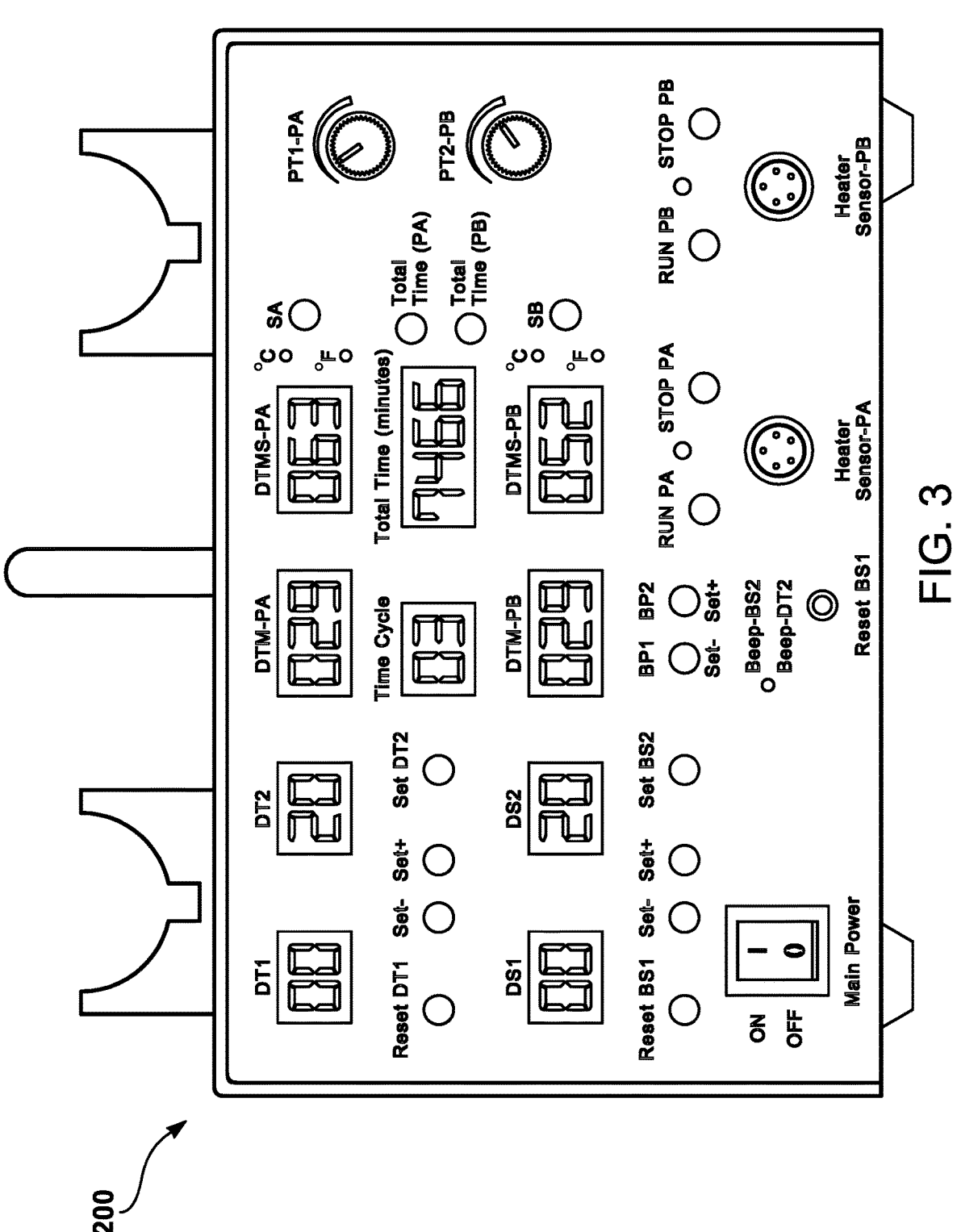
FIG. 3 is a front view the System's Controller, further illustrating the top central handle (for moving the controller) and the two resting-holsters on top (to hold the cubics/probes when not deployed) in one aspect of the invention.

FIG. 3 illustrates the invention's electronic heating box/controller/"unit" 200 from a front view with further defini-tion of pin inputs, switches, dials, lights, settings, alerts and alarms, time readers and controls, set and alert functions, run and cutoff functions, sensor and heater level functions, cutoff functions and readouts for the above. Note that the control unit senses monitors tracks and controls health therapy session times, total unit use time, cycle times, alerts for time frames, and cutoff sensors and functions for the above.

The controller comprises, inter alia, a reset button, a time cycle readout, total time readout, heater sensors PA and PB, Two Alerts Beep readout readings, Five Set (settings), Total Time readout, and PT1-PA and PT2-PB readouts.

Figures 4A, 4B, 4C:
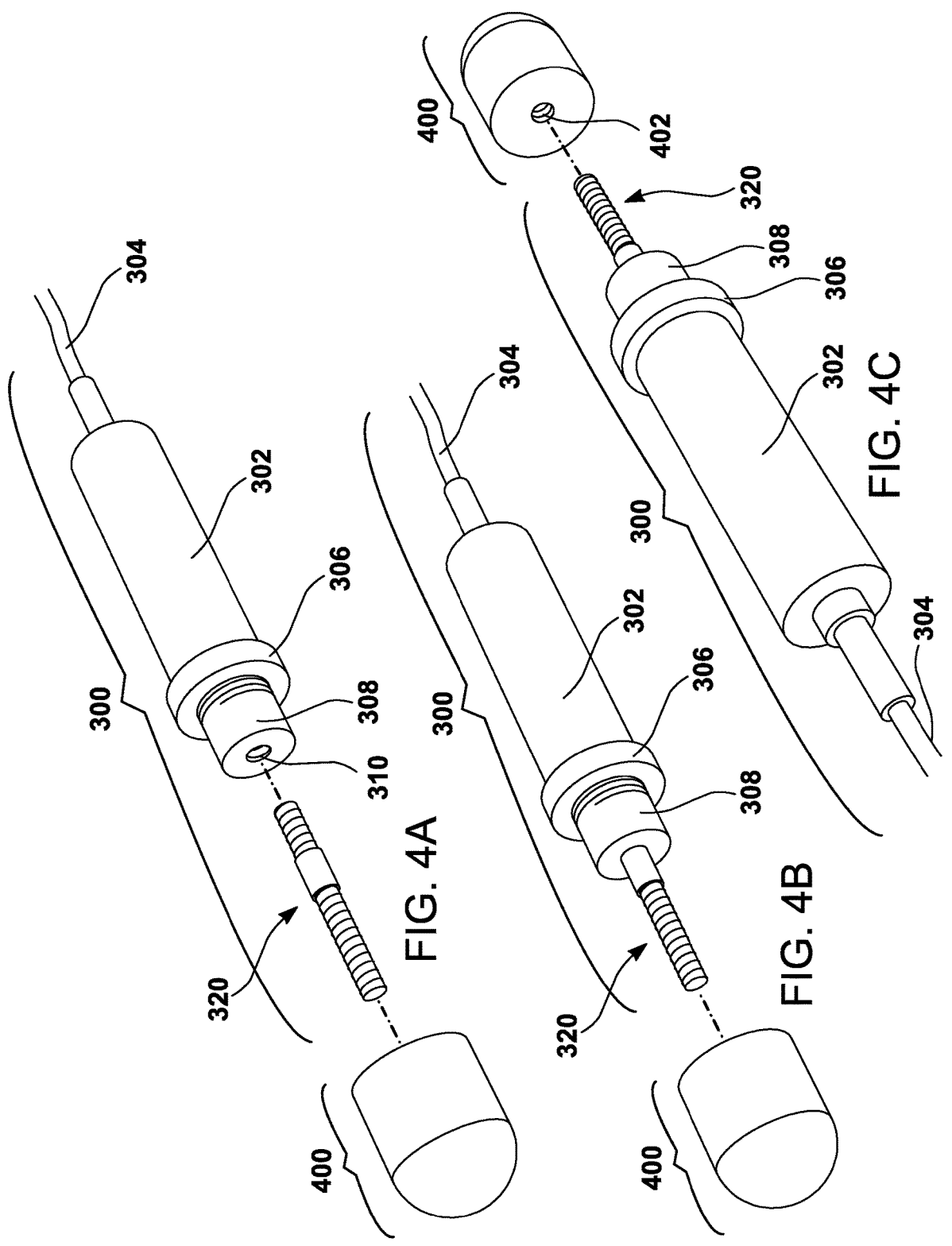
FIG. 4A,B,C are a perspective exploded view of the cubic/probe's various parts/components (both internal and external) in one aspect of the invention.

FIGS. 4A, 4B, 4C are a perspective exploded views of the cubic/probe's various aspects' parts/components (both inter-nal and external) in one aspect of the invention.

FIG. 4A, B, C further illustrate the cord 304 leading to the probe/cubic handle-shaft 302 leading to the sliding-fitting handle rim-collar 306 (used for hand comfort and also to cinch/tighten the sloth probe cover (not herein shown); leading to the threaded handle housing 308, inside which is positioned the internal heating rod 320.

Inter alia, while copper rods are acceptable, amalgam alloys are acceptable; e.g. Nichrome 80/20 is a valid choice for material, because it has relatively high resistance and forms an adherent layer of chromium oxide when it is heated for the first time. The central portion of the internal rod 320 is key because it stops the rod from going too far into the handle housing 308 and too far into the cubic tip 400.

As expected, each cubic tip 400 is internally threaded to house the heating rod element 320, as shown best in FIG. 4C.

Figure 5A:
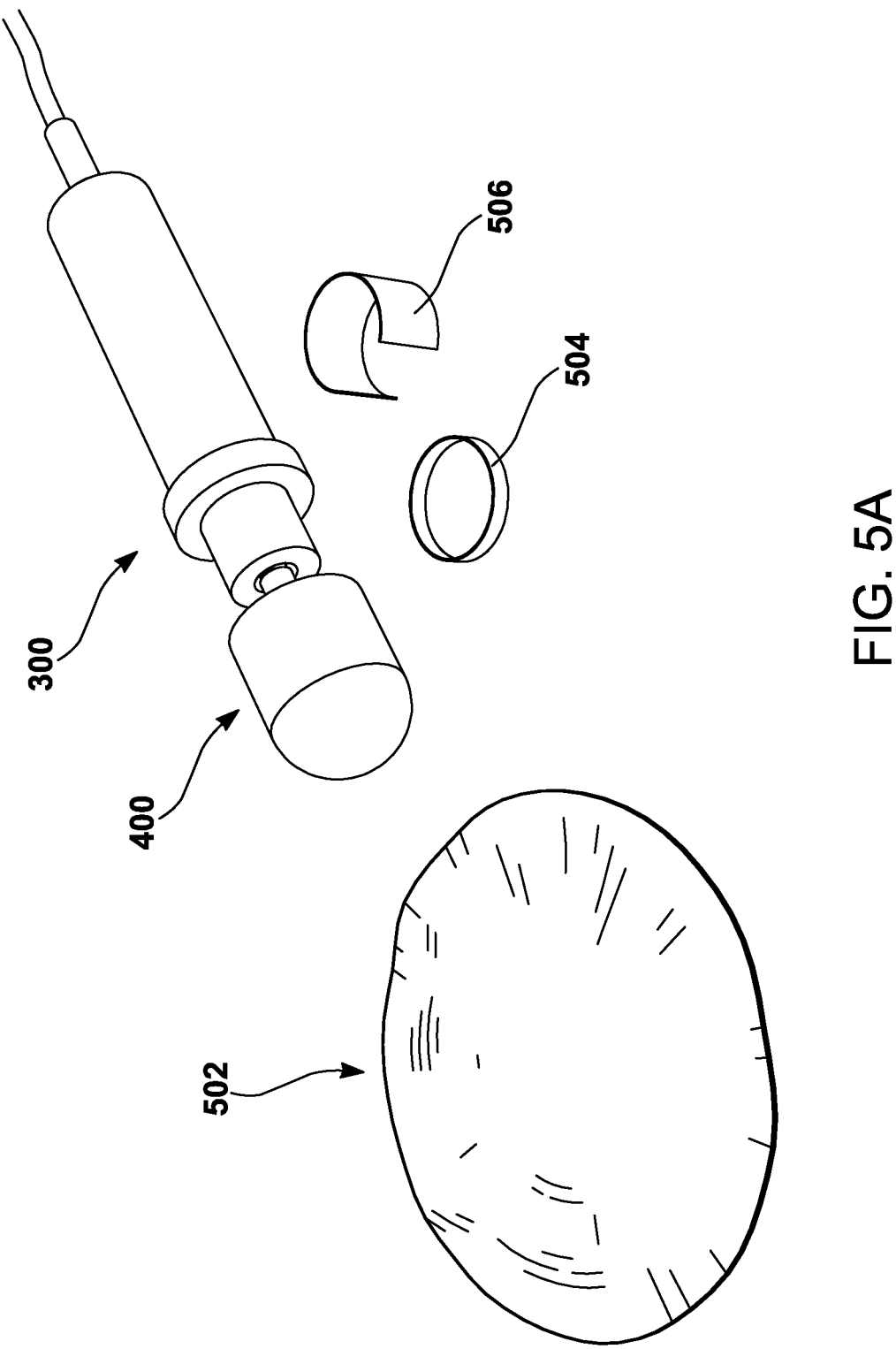
FIG. 5A is a perspective view of the cubic/probe and its cloth cover and collar/elastic-band(s)s in one aspect of the invention.

FIG. 5A features the following materials and components, in one aspect of the invention: the cubic rod/probe 300 whose proximal end has a power cord 304 and whose distal end has a cubic tip 400.

The cinch ring elastic-band 504 is shown here in disas-sembled/exploded fashion, along with the Velro™ cinch piece 506, along with the (herein disassembled) cloth cover 502 for the tip 400.

Best mode materials for these components are as follows:

Disposable Insulative Fabric Cover 502 for, e.g., TSAHP/tip 400;

Elastic Band 504 to Secure Firmly the Insulative Fabric Covers 502

VELCRO 506 style cover/collar/elastic-band(s)/cinch to Double Protect the Insulative Fabric Covers 502

TEFLON (PTFE) THERMAL PROBE—A

TEFLON (PTFE) THERMAL-PROBE—B

Sliding collar 300 to streamline and shore-up the Cover 502 onto the tip 400 while tucking away loose fabric cover 502 material.

Figures 5B, 5C:
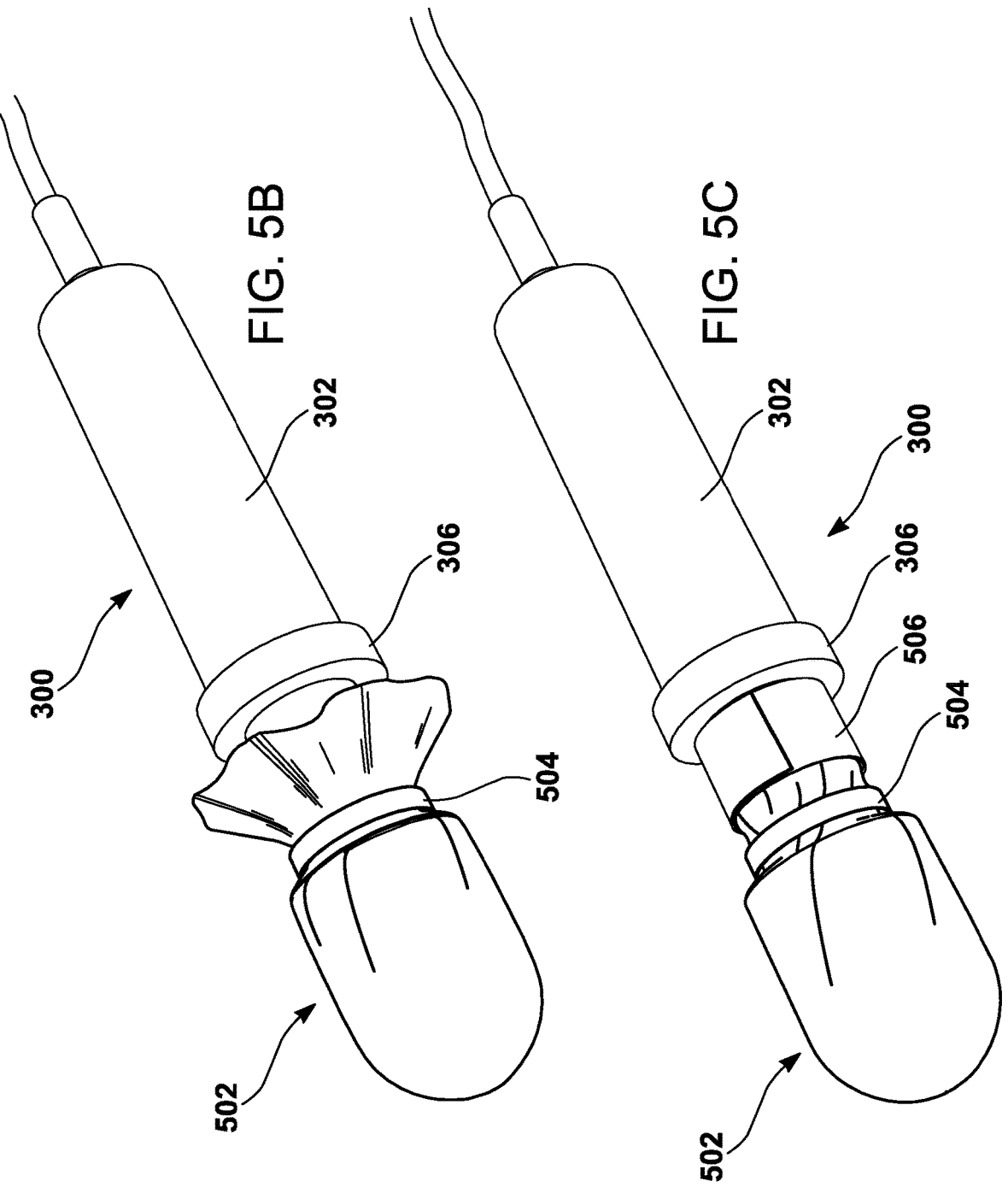
FIG. 5B is a perspective view of the cubic/probe and its cloth cover and collar/elastic-band(s)s attached/assembled in one aspect of the invention.
FIG. 5C is a perspective view of the cubic/probe and its cloth cover and collar/elastic-band(s)s "moved/slid/wrapped" into place for deployment/use.

FIG. 5B illustrates the cubic/probe 300 substantially cinched and ready for use, with various collars, cinches appropriately tightened for safety and efficiency. The figure shows the probe 300 handle 302. The figure also shows the probe collar 306 and tip (covered) safely covered by the disposable cloth 502, which is securely fastened by the elastic band 504.

FIG. 5C shows the cubic/probe fully assembled, cinched and ready for use, featuring the Velcro™-style cinch 506 fastened for tightness, as well as the elastic band 504 positioned for tightness.

Figure 6:
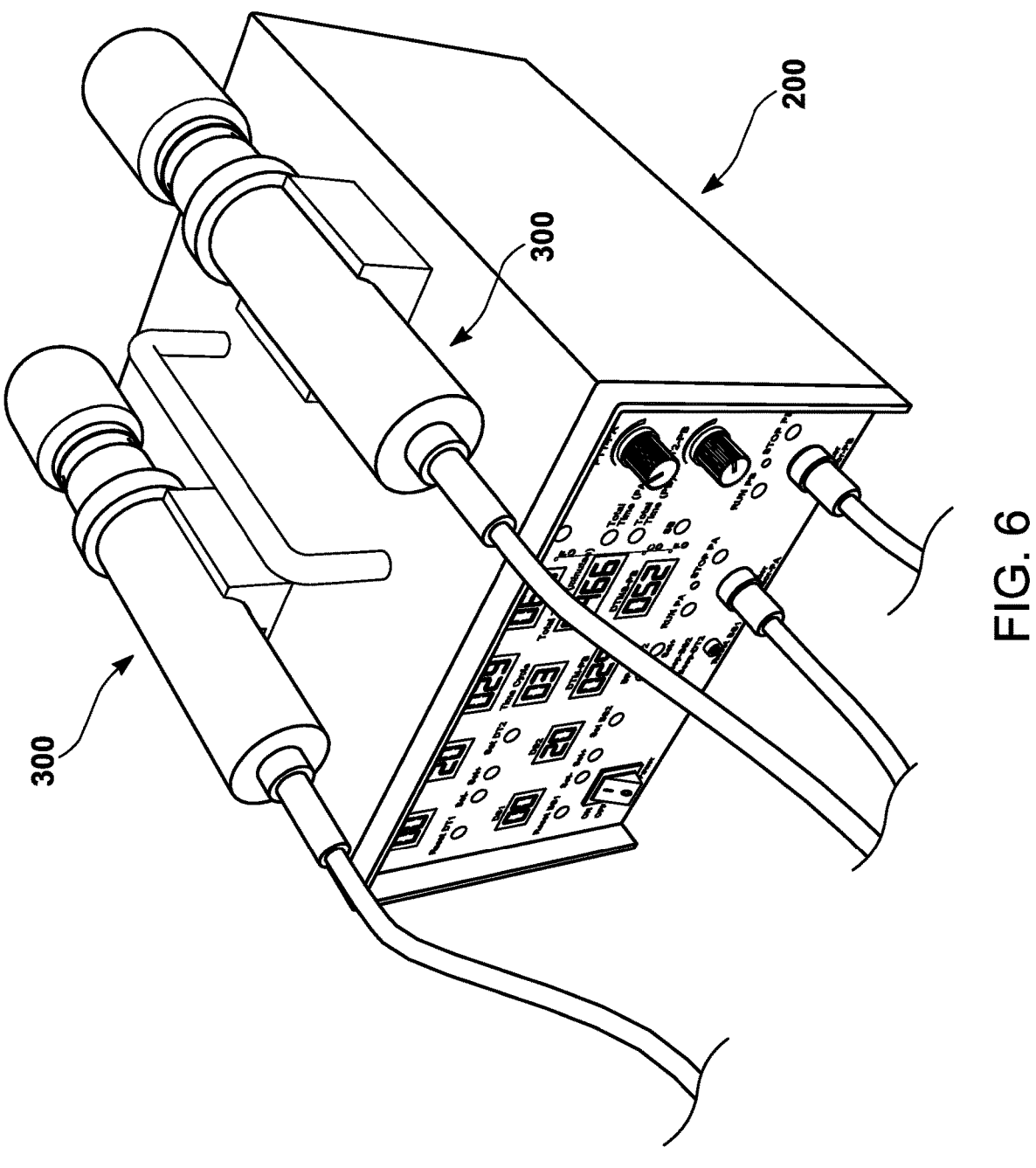
FIG. 6 is a perspective view highlighting the controller with the heat cubics attached/inserted to its two dedicated control channels and the cubics safely resting/housed atop the controller with 'power on,' in one aspect of the invention.

FIG. 6 illustrates the probes/cubics 300 plugged in and safely secured atop the control heating box 200.

Figure 7:
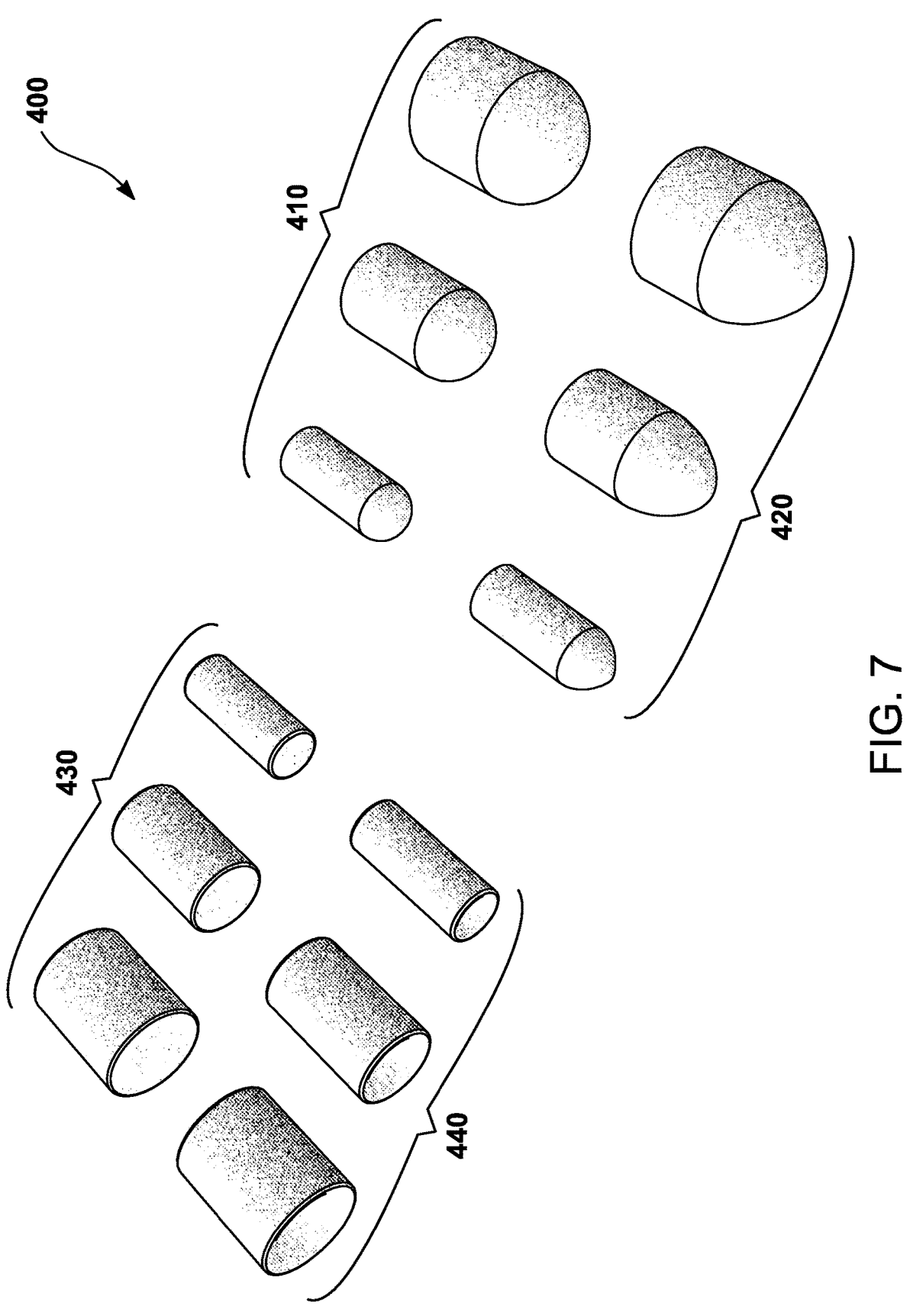
FIG. 7 is a perspective view of the invention's array of cubic heads/tip $400s$/"TSAHPs" ("TSAHP" is an acronym for "Threaded Solid Aluminum Heating Pad,")

FIG. 7 features invention's exemplary array of cubic heads 400/tips/"TSAHPs"

("TSAHP" is an acronym for "Threaded Solid Aluminum Heating Pad,")

(*note that Aluminum can be any appropriate solid material with conductive property, and that Pad can be described as probe/tip 400/head).

Herein (FIG. 7) grouped by head shape (410/420s for convex heads/tip 400s of different diameters; 430s for cubic heads with substantially flat tip 400s [with slight beveled/chamfered edge for comfort] of different sizes/diameters, 440s for tip 400s with concave tip 400s with different sizes/diameters) in one aspect of the invention.

FIG. 7 therefore illustrates the System's Various Shaped/Sized (Internally) Threaded Solid Aluminum Cubics Heating Tip 400s [internal threading shown in FIG. 4C ref. #308).

("TSAHP" is an acronym for "Threaded Solid Aluminum Heating Pad"

Small Concave "TSAHP" Tip 400

Medium Concave "TSAHP" Tip 400

Big Concave "TSAHP" Tip 400

Small Flat "TSAHP" Tip 400

Medium Flat "TSAHP" Tip 400

Big Flat "TSAHP" Tip 400

Small Pointed "TSAHP" Tip 400

Medium Pointed "TSAHP" Tip 400

Big Pointed "TSAHP" Tip 400

Small Round "TSAHP" Tip 400

Medium Round "TSAHP" Tip 400

Big Round "TSAHP" Tip 400

NOTE: USERS CAN QUALIFY WHERE TO USE THESE ALUMINUM CUBICS HEATING PAD DEPENDENT ON THE CONTOUR OF THEIR BODIES, OR WHICH CUBICS THEY ARE CONVENIENT TO USE

FIG. 8 is a perspective view of the sensory rod, the hand-held subject feedback paddle 600, featuring the alarm/beep button 606 and hand grip area 602 and cord 604, in one aspect of the invention. As discussed infra, pushing the button 606 will register a beep with the heater controller 200 and execute the appropriate System responses.

FIG. 9 is a chart describing the System's parameters-prompts illustrating which "TSAHP/cubic tip 400" is applied-to/designed-for which body part, in on aspect of the invention. The TSAHP 400 is correlated with the proper body part for use, as the shape of the TSAHP/cubic tip 400 would indicate:

Small concave tip 400 for fingers, knuckles and toes.

Medium size concave tip 400 for elbow(s), knuckles, and back bone area.

Big concave tip 400 for elbow, knee, shoulder and nape.

Small flat-ended tip 400 (flat distal end/tip/TSAHP 400 of cubic 300) for fingers and toes.

Medium flat tip 400 for face back arms legs.

Big flat tip 400 for back thigh neck arms legs face chest side body and hips.

Small pointed tip 400 for fingers and toes.

Medium pointed tip 400 for neck fingers toes palms and soles of feet.

Big pointed tip 400 for neck, back, thigh, buttocks and hips.

Small rounded tip 400 for neck, fingers, toes, palm and soles of feet.

Medium rounde4d tip 400 for neck arms legs back and chest.

Big round tip 400 for neck arms legs back and chest.

FIG. 10 is a chart describing the System's parameter-prompts-guidelines for proper application of the cubics'/heating probe's 300/400 temperature, time and force (in one aspect of the invention). As the chart shows, for the lowest/first cubic 300 temperature range of about 50 to 55° C., a time range of about 5 to 59 seconds is safe and effective.

(*Note that Controller 200 has DTMS PB with two settings for C. °/F. °).

When the cubic's 300 heat level is set higher via controller 200, the second temp. set to a heat range from 55 to 60° C., a shorter time span is safe and effective, herein between about 5-40 seconds.

When a third temperature range is chosen, between about 60-65° C., a shorter time range is safe and effective, herein between about 5 to 34 seconds. When a fourth/highest temperature range (about 65° C. and about 70° C.) is chosen on the controller 200 for the heating cubic/probe 300, consequently the tip 400 has the highest danger of hurting a human body part if remaining on skin for too long, so the shortest time is used in the System, herein being between about 5 seconds-about 24 seconds.

As also shown in FIG. 10 Chart, While the temp/time settings are part of the System, the application of tip 400 force is also comprised within the System, rising with temperature, said force ranging between about 0.5 lbs of pressure to about 10.5 lbs of pressure depending on the temperature of the tip 400 being applied (and optionally the body part, and the subject feedback paddle 600 and the beep alert button 606. The controller 200 may optionally utilize its automatic cutoff system based on these scenarios, as well as allowing manual control and manual adjustment via the various controller 200 panel controls.

PREFERRED EMBODIMENT/ASPECT

Component Specifications

Disposable Insulative Fabric Cover for TSAHP 400

Elastic Band 504 (to Secure Firmly the Insulative Fabric Covers)

VELCRO Cover 506 (to Double Protect the Insulative Fabric Covers:

TEFLON (PTFE) THERMAL PROBE-A

TEFLON (PTFE) THERMAL-PROBE-B

Controller 200

Main Electrical Plug 120 VAC/240 VAC

Electronic Heating Pad Controller

PTFE (Teflon) Handle Holder

Electronic Controller Panel Holder

Cable A—Female Connector

Cable B—Female Connector

Heater B—Male Connector

Heater A—Male Connector

Cable A—Female Connector to the

Cartridge Heater A

Cable B—Female Connector to the

Cartridge Heater B

Heater Handle B—Male Connector

Heater Handle A—Male Connector

PTFE (Teflon) Handle for the Aluminum

Heating Cubics Pad—A

PTFE (Teflon) Handle for the Aluminum

Heating Cubics Pad—B

Threaded Aluminum Heated Tip 400-A—To screw the solid aluminum cubics heating pad Threaded Aluminum Heated Tip 400-B—To screw the the solid aluminum cubics heating pad Manual Push Button-Rest (MPBR)

MPBR—Female Connector

MPBR—Male Connector

O-Ring—A Hand Stopper

O-Ring—B Hand Stopper.

EXEMPLARY STEPS FOR SYSTEM

Heat Therapy System'S Procedure and Methodology

NOTE: AFTER CONNECTING ALL THE NECESSARY CABLES, CONNECTORS A & B AND CONSUMABLES TO THE PTFE THERMAL PROBES A&B PER PROPER SETUP OF THE DEVICE:

1. SWITCH ON THE MAIN POWER
2. SET DT2 TO DESIRED TIME TO AUTOMATICALLY SHUT OF HEATER/SENSOR PA AND HEATER/SENSOR PB, SETTING IS FROM 01 TO 99 MINUTES, INITIALLY SET THE DT2 TO 60 MINUTES USING THE SET DT2. SET– AND SET+ BUTTONS, THEN THE AUTOMATIC SHUT OFF IS SET AT 60 MINUTES.
3. SET TEMPERATURE OF HEATER/SENSOR PA BY SETTING DTMS-PA USING THE PT1-PA KNOB TO SET THE TEMPERATURE, SET INITIALLY THE TEMPERATURE TO SAY 59 DEGREES ° C. (SUGGESTED INITIAL SETTING CAN BE FROM 55 DEGREES ° C. TO 62 DEGREES ° C.)
4. THEN PUSH RUN PA BUTTON TO START ENERGIZING THE HEATER/SENSOR PA. THIS TIME HEATER/SENSOR PA IS RUNNING
5. SET TEMPERATURE OF HEATER/SENSOR PB BY SETTING DTMS-PB USING THE PT2-PB KNOB TO SET THE TEMPERATURE, SET INITIALLY THE TEMPERATURE TO SAY 59 DEGREES ° C. (SUGGESTED INITIAL SETTING CAN BE FROM 55 DEGREES ° C. TO 62 DEGREES ° C.)
6. THEN PUSH RUN PB BUTTON TO START ENERGIZING THE HEATER/SENSOR PB. THIS TIME HEATER/SENSOR PA IS RUNNING
7. BOTH HEATER/SENSOR PA AND HEATER/SENSOR PB ARE RUNNING
8. NOTE: IT WILL TAKE APPROXIMATELY FIVE (5) MINUTES FOR HEATER/SENSOR PA AND HEATER SENSOR PB, THEN BOTH ARE READY TO BE USED
9. USE THE DIGITAL WEIGHING SCALE TO CALIBRATE WHAT PRESSURE BY WEIGHT IN POKING THE PTFE PROBE TO THE BODY. SUGGESTED INITIAL PRESSURE IS FROM 3 LBS TO 5 LBS
10. SAY PTFE THERMAL PROBE-A IS USING THE BIG FLAT CUBIC TIP 400 (BFCT) WHILE THE PTFE THERMAL PROBE-BIS USING THE BIG POINTED CUBIC TIP 400 (BPCT)
11. SAY. YOU WILL BE USING THE INVENTION DEVICE FOR UPPER BACK PAIN, INITIALLY USE THE BFCT TO POKE AT THE FLAT SURFACE AT BACK TO WHERE THE PAIN IS, WHEN THE

PERSON UNDER THERAPY AT CERTAIN POKING TIME FEELS HEATED UP, TABULATE THE TIME ELAPSED

12. ASK THE PERSON UNDER THERAPY IF THE SET TEMPERATURE AND PRESSURE IS ACCEPTABLE TO HIS/HER SENSITIVITY (WHEN SHE/HE FEELS THE HEAT IS HIGH THEN REDUCE THE TEMPERATURE SETTING DTMS-PA OR DTMS-PB BY 2 DEGREES ° C., THEN WHEN TEMPERATURE IS SATURATES AT THE NEW SET TEMPERATURE. THEN REPEAT THE POKING UNTIL THE TEMPERATURE IS AT THE DESIRED SENSITIVITY OF THE PERSON UNDER THERAPY)
13. NOTE: DURING THERAPY. THE PERSON UNDER THERAPY WILL HOLD THE MANUAL PUSH BUTTON RESET (MPBR). THAT WHENEVER HE/SHE FEELS HEATED UP DURING POKING OF THE PTFE PROBE, HE/SHE WILL PUSH THE MPBR TO TRIGGER THE BEEPING THUS SIGNALLING TO THE PERSON DOING THE THERAPY TO MOVE THE PROBE TO OTHER SPOT
14. TABULATE THE CALIBRATED AND DESIRED TEMPERATURE, TIME AND PRESSURE USED
15. POKE THE PTFE PROBE COVERED CUBIC PAD DIRECTLY TO THE BODY SKIN TO WHERE THE PAIN IS (MAKE SURE THAT THE FABRIC COVER OF THE CUBICS PAD DOES NOT HAVE A HOLE OR DEFECT ON IT BEFORE POKING TO AVOID BLISTERING ON THE SKIN))
16. WHEN THE PTFE PROBE COVERED ALL THE BODY PAIN ISSUES YOU CAN REPEAT THE POKING AT THE SAME PREVIOUS SPOTS (2 TO 3 TIMES MORE) WHERE THE PTFE PROBE HAS BEEN POKED UNTIL SIGNIFICANT REDUCTION OF PAIN HAS BEEN ATTAINED
17. REMINDER: CALIBRATE PROBE 1 & PROBE 2 TEMPERATURE, PRESSURE AND TIME IN ACCORDANCE TO SKIN SENSITIVITY TO HEAT OF THE PERSON WHO WILL USE THE DEVICE;
   A. POKE THE PROBE A OR B TO THE DESIRED PART OF THE BODY (BUT ONE PROBE A TA TIME)
   B. CALIBRATE THE TEMPERATURE SETTING (LOG THE DATA)
   C. CALIBRATE THE PRESSURE (LOG THE DATA)
   D. CALIBRATE THE TIME (LOG THE DATA)
      NOTE: CALIBRATE AND TABULATE DATA REFERENCING THE ATTACHED: 1. HEAT THERAPY CALIBRATION SHEET, 2. FIG. FB-01. FRONTAL BODY CALIBRATION POINTS, 3. FIG. BB-02-BACK BODY CALIBRATION POINTS, 4. PHOTO01. POKING PRESSURE CALIBRATOR, 5. TEMP. VS. TIME VS. PRESSURE SETTING CALIBRATION CHART
   E. ONCE THE TEMPERATURE, PRESSURE AND TIME SETTING HAS BEEN ESTABLISHED. REMEMBER SAID DATA IN POKING THE PTFE THERMAL PROBE CUBICS HEATED PAD TO THE PERSON'S SPECIFIC BODY PARTBODY. THAT CAN BE HIS/HER SETTING POINTS WHENEVER USING AGAIN THE HEAT DEVICE
18. BE SURE TO REMOVE THE POKED CUBICS HEATED PAD WHEN THE PERSON UNDER

THERAPY FEELS HEATED UP ALREADY THEN MOVE TO OTHER BODY PARTS THAT IS WITH PAIN ISSUE

19. REPEAT THE POKING TO THE DIFFERENT PARTS OF THE BODY UNTIL COVERING ALL THE SPECIFIC BODY PAIN COMPLAINT. BUT TAKE NOTE USING THE CALIBRATION TEMPERATURE, TIME AND PRESSURE

20. THE DEVICE WILL ONLY TEMPORARILY ALLEVIATE MUSCLE PAIN, IF MUSCLE PAIN PERSIST, DISCONTINUE USE AND CONSULT YOUR DOCTOR

Suggested Setting Parameters

1. STANDARD AVERAGE TEMPERATURE SETTING IS FROM 50 DEGREES ° C. TO 70 DEGREES ° C.

2. STANDARD AVERAGE PRESSURE SETTING (IN WEIGHT) IS FROM ONE (1) POUND TO SEVEN (7) POUNDS

3. STANDARD AVERAGE TIME SETTING FOR POKING THE PROBE IS FROM FIVE (5) SECONDS TO TWENTY-FIVE (35) SECONDS

4. PLEASE BE AWARE THAT DIFFERENT INDIVIDUAL DIFFERS IN THEIR TEMPERATURE, TIME AND PRESSURE SETTINGS

5. CALIBRATION WILL BE DONE BY PROPERLY TRAINED PERSONNEL.

Specifications Generally

In the Summary above and in this Detailed Description, and the Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments. elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used.

Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112(f). Specifically, any use of "step of" in the claims herein is not intended to invoke the provisions of 35 U.S.C. § 112(f). Elements recited in means-plus-function format are intended to be construed in accordance with 35 U.S.C. § 112(f).

Recitation in a claim of the term "first" with respect to a feature or element does not necessarily imply the existence of a second or additional such feature or element.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

What is claimed is:

1. A heat-pressure body therapy system comprising:
a grounded electronic controller with a top end and a bottom end,
the controller comprising:
at least one thermocouple sensor for each of two handheld probes;
wherein the following components are connected to the controller:
at least one handheld feedback paddle comprising at least one discomfort button,
two handheld probes with threaded centers for attachment of a plurality of detachable metallic tips,
the plurality of detachable metallic tips includes tips having varying diameters,
two cloth covers, one such cover for each probe tip,
two identical cinch collars, each collar securing one cloth cover to its matching probe tip,
wherein the covered probes are configured to be heated to a temperature between about 550 ° C. to about 62° C.,
the covered probes are configured to be pressed against human skin with a force of between about 3 lbs. of pressure to about 5 lbs. of pressure for a period of between 5 seconds and about 35 seconds,
wherein the controller is configured to instantly terminate heat delivery to the probes upon any activation of the discomfort button on the feedback paddle during application, thereby ending the heated-pressure therapy session.

* * * * *